(12) United States Patent
Meyer-Boehm et al.

(10) Patent No.: US 10,835,456 B2
(45) Date of Patent: Nov. 17, 2020

(54) PROPYL GALLATE-CONTAINING VITAMIN PREPARATIONS

(71) Applicant: BASF SE, Ludwigshafen am Rhein (DE)

(72) Inventors: Kathrin Meyer-Boehm, Ludwigshafen am Rhein (DE); Thrandur Helgason, Illertissen (DE); Raajvinder Singh, Ludwigshafen am Rhein (DE); Walter Dobler, Ludwigshafen am Rhein (DE); Peter Schording, Bubenheim (DE); Christof Wilhelm Wigbers, Ludwigshafen am Rhein (DE); Karl Kolter, Ludwigshafen am Rhein (DE); Stefan Bruhns, Ludwigshafen am Rhein (DE); Wolf Pelletier, Lampertheim (DE); Daniel Wagner, Lampertheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 16/316,802

(22) PCT Filed: Jul. 17, 2017

(86) PCT No.: PCT/EP2017/068038
§ 371 (c)(1),
(2) Date: Jan. 10, 2019

(87) PCT Pub. No.: WO2018/015346
PCT Pub. Date: Jan. 25, 2018

(65) Prior Publication Data
US 2019/0240119 A1 Aug. 8, 2019

(30) Foreign Application Priority Data
Jul. 19, 2016 (EP) .................................. 16180199

(51) Int. Cl.
| | | |
|---|---|---|
| *A61K 8/02* | (2006.01) | |
| *A23K 20/174* | (2016.01) | |
| *A23P 10/20* | (2016.01) | |
| *A23L 33/155* | (2016.01) | |
| *A61K 31/12* | (2006.01) | |
| *A61K 31/122* | (2006.01) | |
| *A61K 31/355* | (2006.01) | |
| *A61K 8/67* | (2006.01) | |
| *A61Q 19/00* | (2006.01) | |
| *A61K 8/31* | (2006.01) | |
| *A61K 45/06* | (2006.01) | |
| *A61K 31/015* | (2006.01) | |
| *A23L 33/15* | (2016.01) | |
| *A61K 31/235* | (2006.01) | |
| *A61K 8/34* | (2006.01) | |
| *A61K 8/35* | (2006.01) | |
| *A61K 8/37* | (2006.01) | |
| *A61K 9/14* | (2006.01) | |
| *A61K 31/05* | (2006.01) | |
| *A61K 31/375* | (2006.01) | |

(52) U.S. Cl.
CPC ............ *A61K 8/022* (2013.01); *A23K 20/174* (2016.05); *A23L 33/15* (2016.08); *A23L 33/155* (2016.08); *A23P 10/20* (2016.08); *A61K 8/31* (2013.01); *A61K 8/347* (2013.01); *A61K 8/35* (2013.01); *A61K 8/37* (2013.01); *A61K 8/67* (2013.01); *A61K 8/676* (2013.01); *A61K 8/678* (2013.01); *A61K 9/14* (2013.01); *A61K 31/015* (2013.01); *A61K 31/05* (2013.01); *A61K 31/12* (2013.01); *A61K 31/122* (2013.01); *A61K 31/235* (2013.01); *A61K 31/355* (2013.01); *A61K 31/375* (2013.01); *A61K 45/06* (2013.01); *A61Q 19/00* (2013.01); *A23V 2002/00* (2013.01); *A61K 2800/10* (2013.01); *A61K 2800/412* (2013.01); *A61K 2800/52* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 2,756,177 | A | 7/1956 | Cannalonga et al. |
| 6,093,348 | A * | 7/2000 | Kowalski ............... A61K 9/145 |
| | | | 106/498 |
| 6,296,877 | B1 | 10/2001 | Auweter et al. |
| 9,617,502 | B2 | 4/2017 | Loughnane et al. |
| 9,981,904 | B2 | 5/2018 | Wigbers et al. |
| 10,150,746 | B2 | 12/2018 | Fischer et al. |
| 10,188,133 | B2 | 1/2019 | Gierke et al. |
| 10,280,237 | B2 | 5/2019 | Vacano et al. |

(Continued)

FOREIGN PATENT DOCUMENTS

| | | |
|---|---|---|
| CA | 2360727 A1 | 8/2000 |
| CN | 102657663 B | 5/2013 |

(Continued)

OTHER PUBLICATIONS

Database WPI Week 201306, Thomson Scientific, London, GB An 2012-R30178.

(Continued)

*Primary Examiner* — Celeste A Roney
(74) *Attorney, Agent, or Firm* — Faegre Drinker Biddle & Reath LLP

(57) ABSTRACT

The present invention relates to a pulverulent vitamin formulation in which the vitamin essentially has a particle size of less than 0.7 μm and which comprises an effective amount of propyl gallate, and also to processes for producing this formulation, and to formulations obtainable by these processes and to the use thereof as animal feed, food, food supplement, personal care product or pharmaceutical composition. The formulations of the invention have improved stability compared to the prior art.

11 Claims, No Drawings

(56) References Cited

U.S. PATENT DOCUMENTS

| | | | |
|---|---|---|---|
| 2006/0035871 A1* | 2/2006 | Auweter | A61K 8/02 514/169 |
| 2017/0362164 A1 | 12/2017 | Wigbers et al. | |
| 2018/0228730 A1 | 8/2018 | Schiffier et al. | |
| 2018/0235885 A1 | 8/2018 | Schiffter et al. | |
| 2018/0305636 A1 | 10/2018 | Kolter et al. | |
| 2018/0317523 A1 | 11/2018 | Helgason et al. | |
| 2019/0060209 A1 | 2/2019 | Kolter et al. | |
| 2019/0090529 A1 | 3/2019 | Meyer-Boehm et al. | |
| 2019/0099371 A1 | 4/2019 | Hansen et al. | |

FOREIGN PATENT DOCUMENTS

| | | |
|---|---|---|
| DE | 19651681 A1 | 6/1998 |
| DE | 19903716 A1 | 8/2000 |
| DE | 69728206 T2 | 3/2005 |

OTHER PUBLICATIONS

J.D. Dziezak, "Preservatives: Antioxidants. The Ultimate Answer to Oxidation", Food Technology, 1986, vol. 40, Issue 9, pp. 94-102.
International Search Report for PCT/EP2017/068038 dated Sep. 21, 2017.
Written Opinion of the International Searching Authority for PCT/EP2017/068038 dated Sep. 21, 2017.

* cited by examiner

PROPYL GALLATE-CONTAINING VITAMIN PREPARATIONS

CROSS-REFERENCE TO RELATED APPLICATIONS

This application is a national stage application (under 35 U.S.C. § 371) of PCT/EP2017/068038, filed Jul. 17, 2017, which claims benefit of European Application No. 16180199.8, filed Jul. 19, 2016, both of which are incorporated herein by reference in their entirety.

The present invention relates to a formulation having antioxidant properties, and to the production and use thereof.

A difficulty in the production of vitamin-containing formulations is that they are often unstable and are damaged by oxidative processes both during the production process and in the course of subsequent storage or further processing in premixes, pellets or feeds. The damage can be caused by reaction with atmospheric oxygen or interactions with heavy metals or by the absorption of UV radiation. As a result of the damage caused thereby, the vitamins can, for example, change color and/or lose efficacy.

A known way of addressing the problems described involves an addition of antioxidants to the formulations.

According to CD Römpp Chemie Lexikon 10th edition, Version 1.3, Stuttgart/New York: Georg Thieme Verlag, antioxidants are compounds that inhibit or prevent unwanted changes caused by effects of oxygen, including oxidative processes, in the substances to be protected.

Ethoxyquin has antioxidant action and hence protective action in vitamins. The toxicological data position for ethoxyquin is inadequate; the substance ethoxyquin itself is considered to be non-genotoxic. However, the European Food Safety Authority (EFSA) has determined that one of its metabolites, ethoxyquin quinone imine, is potentially genotoxic (i.e. DNA-damaging), which suggests possible safety concerns.

As a result of the process for preparing ethoxyquin, there is additionally an impurity, p-phenetidine, which is possibly a mutagen, that remains in the animal feed. Mutagens are substances that trigger mutations in the human and animal phenotype.

Owing to the current unavailability of data, the EFSA is not able to determine the safety of ethoxyquin as animal feed additive for the target animals, or to make a conclusive assessment of safety for consumers or the environment.

Owing to these safety concerns, there is an acute need for antioxidants that are suitable for use as additives for animal feeds, foods, food supplements, personal care products or pharmaceutical compositions and can replace ethoxyquin in its formulations in the short term.

It is therefore an object of the invention to provide a formulation that achieves or surpasses the stabilities of ethoxyquin-comprising formulations without triggering the safety concerns that exist for ethoxyquin.

It has been found here that, surprisingly, a pulverulent vitamin formulation in which the vitamin essentially has a particle size of less than 0.7 µm and which comprises an effective amount of propyl gallate is of excellent suitability for achieving the stated object.

According to the invention, an effective amount of propyl gallate is understood here to mean the amount of propyl gallate suitable for stabilizing the vitamin in the formulation such that, after 4 weeks in the stress test, at least 20% by weight of vitamin, preferably at least 25% by weight and especially preferably at least 30% by weight of the vitamin content present at the start of the stress test is still conserved.

The stress test for the vitamins is configured such that specimens of 100 mg in each case of the formulation produced and 4 g of premix mixture are weighed into glass vessels. The premix mixture consists of 50% by weight of fine lime (particle size <1000 µm), 20% by weight of wheat bran (particle size <1000 µm), 20% by weight of 50% silica-supported choline chloride (particle size <1000 µm) and 10% by weight of trace element mixture (particle size 100-500 µm). The trace element mixture is composed of 46.78% by weight of $FeSO_4 \times 7H_2O$ (100-500 µm), 37.43% by weight of $CuSO_4 \times 5H_2O$ (100-500 µm), 11.79% by weight of ZnO (<500 µm), 3.61% by weight of MnO and 0.39% by weight of $CoCO_3$. After addition of all ingredients, the specimens are mixed cautiously, with performance of the mixing mechanically or else by hand, and these specimens (A) are stored in a climate-controlled chamber at 40° C. and 70% humidity for 4 weeks. Prior to commencement of the storage and on conclusion of the storage, the vitamin content of the specimens is determined. The ratio of the contents after (A2) and before the storage (A1) are used to calculate the retention (A2/A1) of the samples, i.e. the vitamin content still present in the specimens.

In particular, an effective amount of propyl gallate is understood to mean 3.5% to 9.5% by weight of propyl gallate, preferably 4% to 9% by weight, more preferably 7% to 9% by weight and especially 8% to 9% by weight of propyl gallate, based on the total amount of the formulation in the production step, where the sum total of the percentages by weight of the components is 100% by weight and where the weight ratio of propyl gallate to vitamin in the production is between 0.21 and 2.63.

According to the invention, the term "production step" Includes all process steps a1 to c1 or a2 to c2 or a3 to c3 until the desired process product is obtained.

It should be explicitly emphasized that, in this application, all figures of amount and concentration and relative ratios, irrespective of whether they relate to the pulverulent formulation or the solution or dispersion, relate to the amounts used in the production step, since both propyl gallate and tocopherol or butylhydroxytoluene (BHT), as antioxidants, in the course of production but also in the course of storage or further processing, are subject to a constant degradation process, and it is therefore reliably possible to put a number on the content thereof in the formulation only for the commencement of the production, in the weighing operation.

In the context of the present invention, a dispersion means either emulsion or suspension.

What is meant or encompassed by the term "essentially" in the context of this invention is more particularly that not less than 80 percent, more preferably not less than 85 percent, further preferably not less than 90 percent and most preferably not less than 95 percent of the particles formed in the dissolution of the pulverulent vitamin formulations have a particle size of less than 0.7 µm.

The particle size is determined by means of a Malvern Zetasizer Nano ZSP.

According to the invention, preferred vitamins are vitamins selected from the group of vitamins D, E, K or Q or derivatives thereof, for example vitamin E esters such as tocopherol acetate, tocotrienol, vitamin K1, vitamin K2, coenzyme Q10 and carotenoids such as n-carotene, canthaxanthin, citranaxanthin, astaxanthin and ester derivatives, zeaxanthin and ester derivatives, lutein and ester derivatives, lycopene, apocarotenic acid and ester derivatives, apocarotenal and mixtures thereof.

The coherent phase present in the vitamin formulation of the invention is at least one colloid selected from the group consisting of plant gums, modified plant gums, gelatin, modified gelatin, modified starch, lignosulfonate, chitosan, carrageenan, casein, caseinate, whey protein, zein, modified cellulose, pectin, modified pectin, plant proteins and modified plant proteins or mixtures thereof.

According to the invention, plant gums are understood here to mean agar, alginic acid, alginate, chicle, dammar, marshmallow extracts, gellan, guar flour, gum arabic, gum from plantain seed husk, gum from spruce tree sap, carob flour, karaya, konjac flour, mastic, tara gum, tragacanth, xanthan.

According to the invention, preferred coherent phases are gelatin and/or plant gums and/or modified plant gums.

It has likewise been found that, surprisingly, an addition of tocopherol or BHT to the formulation promotes or enhances the antioxidant protective effect of propyl gallate in the formulation by a synergistic mode of action. According to the invention, tocopherol is understood to mean either natural or synthetic tocopherol. Natural tocopherol is understood to mean the naturally occurring α-, β-, γ-, λ-tocopherols, which are also embraced by the term "mixed tocopherols" and are sold by BASF under the Covi-OX brand name. Synthetic tocopherol, also called DL-α-tocopherol, by contrast, contains a random mixture of the eight α-diastereomers. In the case of addition of tocopherol to the formulation, preference is given in accordance with the invention to the addition of natural tocopherol.

Preference is given in accordance with the invention to formulations in which propyl gallate and tocopherol are present in a relative weight ratio of 9:1 to 1:2, particular preference being given to a relative ratio of the two antioxidants of 2:1 to 1:1.

Preference is given in accordance with the invention to formulations in which the antioxidant protective action of propyl gallate is promoted or enhanced by addition of butylhydroxytoluene (BHT) when they are present in a weight ratio of propyl gallate to BHT of 8:1 to 1:4, more preferably when they are present in a weight ratio of 2:1 to 1:3.

The advantage of the formulation of the invention lies particularly in its antioxidant action which, by comparison with the formulations comprising ethoxyquin or other customary antioxidants, is manifested in a comparable, especially improved, stability of the vitamins in the formulations of the invention.

The comparable or improved stability of the vitamin formulations of the invention can be demonstrated by a stress test. For this purpose, specimens each of 100 mg of the formulation produced and 4 g of premix mixture are weighed out in glass vessels (50 mL glass vials). The premix mixture consists of 50% by weight of fine lime (particle size <1000 μm), 20% by weight of wheat bran (particle size <1000 μm), 20% by weight of 50% silica-supported choline chloride (particle size <1000 μm) and 10% by weight of trace element mixture (particle size 100-500 μm), said trace element mixture consisting of 46.78% by weight of $FeSO_4 \times 7H_2O$ (100-500 μm), 37.43% by weight of $CuSO_4 \times 5H_2O$ (100-500 μm), 11.79% by weight of ZnO (<500 μm), 3.61% by weight of MnO and 0.39% by weight of $CoCO_3$. After addition of all ingredients, the specimens are mixed cautiously, where the mixing can be performed mechanically or else by hand, and these specimens (A) are stored in a climate-controlled chamber at 40° C. and 70% humidity for 4 weeks. An identical test is conducted with a comparative sample (B) which is of identical composition but which comprises, rather than propyl gallate, the same amount of ethoxyquin. Prior to commencement of the storage and on conclusion of the storage, the vitamin content of the specimens is determined here. The ratio of the contents after (A2), (B2) and before the storage (A1) and (B1) are used here to calculate the retention (A2/A1) or (B2/B1) of the samples. For the formulations of the invention, a quotient (A2/A1):(B2/B1) of at least 0.75 is determined here. Preferably, for the formulations of the invention, a quotient of at least 1 is obtained.

For improvement of the production and the performance properties of the vitamin formulation, it may be appropriate to add further components, such as plasticizers and further auxiliaries and additives. Preferred auxiliaries and additives are emulsifiers, oils, water-soluble salts and/or separating agents.

To adjust the mechanical stability of the coherent phase of the vitamin formulation, it is appropriate to add at least one plasticizer to the colloid, such as polyols, sugars or sugar alcohols, e.g. sucrose, glucose, glucose syrup, starch hydrolyzates, fructose, fructose syrup, lactose, maltose, xylose, arabinose, ribose, trehalose, invert sugar, sorbitol, mannitol, dextrin, maltodextrin, glycerol, polyether glycols or isomalt. The name isomalt denotes a sugar substitute which is also supplied under the Palatinit® tradename (Südzucker, Germany). Isomalt is a hydrogenated isomaltulose which consists of roughly equal portions of 6-O-α-D-glucopyranosyl-D-sorbitol and 1-O-α-D-glucopyranosyl-D-mannitol. Plasticizers used with preference are sucrose, glucose syrup and lactose.

Further auxiliaries and additives used may be emulsifiers to stabilize the phases in the production of the vitamin formulation of the invention, for example mono- and diglycerides, monoglycerol fatty acid esters, polyglycerol fatty acid esters, sorbitan fatty acid esters, propylene glycol fatty acid esters, monoglycerol citric acid esters, sugar fatty acid esters or lecithin. Emulsifiers used with preference are mono- and diglycerides, monoglycerol fatty acid esters and lecithin.

Under some circumstances, it may also be advantageous additionally to use a physiologically approved oil of animal or vegetable origin, for example sesame oil, maize kernel oil, cottonseed oil, soybean oil, peanut oil, sunflower oil, rapeseed oil, coconut oil, palm oil, olive oil, safflower oil, animal fats, lard, tallow, oils modified by hydrogenating, fractionating or transesterifying, or mixtures. Preferred oils are maize kernel oil, sunflower oil and rapeseed oil.

In addition, metal chelators, such as EDTA and citric acid, may also be added to the vitamin formulation of the invention.

In addition, water-soluble inorganic and/or organic salts may advantageously also be added for the coherent phase of the vitamin formulation, for example sodium ascorbate, potassium ascorbate, calcium ascorbate, sodium erythorbate, potassium erythorbate, sodium benzoate, potassium benzoate, sodium citrate, potassium citrate, alkali metal phosphates, alkali metal acetates, alkali metal phytates and mixtures thereof. Preferred salts are sodium benzoate and disodium hydrogenphosphate.

In order to avoid unwanted lump formation and to improve flowability, sparingly water-soluble, finely particulate separating agents having average particle sizes of not more than 10 μm (×50.3 according to DIN ISO 9276-2: 2006-02) are appropriately added, and these accumulate on the surface of the pulverulent vitamin formulation. The preferred separating agent is selected from the group consisting of silicon dioxide, hydrophobically modified silica, tricalcium phosphate (TCP), calcium carbonate, sodium carbonate, potassium carbonate, magnesium carbonate, calcium oxide, magnesium oxide, dicalcium diphosphate, calcium silicate, magnesium silicate, magnesium trisilicate, sodium aluminum silicate, talc, kaolin, calcium stearate, magnesium stearate, starches from different botanical sources, cellulose or mixtures thereof.

Particular preference is given here to silicon dioxide, tricalcium phosphate (TCP), hydrophobically modified silica and cornstarch.

According to the invention, the proportion of auxiliaries and additives is 0.1% to 60% by weight, preferably 1% to 50% by weight and more preferably 5% to 30% by weight, based on the total amount of the formulation in the production step, where the sum of the percentages by weight of all components of the formulation is 100% by weight.

The invention further provides a process for producing the pulverulent formulation described above, comprising
- a1) the dissolving of the vitamin in a volatile, water-miscible organic solvent or in a mixture of water and a water-miscible organic solvent at temperatures between 50° C. and 200° C., optionally under elevated pressure between 20 bar and 100 bar, within a period of less than 10 seconds,
- b1) the rapid mixing of the solution obtained after a1) with an aqueous or colloidally dispersed solution of a colloid at temperatures between 0° C. and 80° C., with precipitation of the vitamin in colloidally dispersed form,
- c1) the conversion of the dispersion formed to a dry powder by removing the majority of solvent and subsequent drying.

The process is performed in the presence of propyl gallate as antioxidant, which is added in an effective amount in accordance with the invention. Preference is given to adding 3.5% to 9.5% by weight of propyl gallate to the production process based on the total amount of the formulation, where the weight ratio of propyl gallate to vitamin in the production is between 0.21 and 2.63. The propyl gallate can be added to process steps a1) and/or b1) and/or c1), preference being given to the addition of the propyl gallate in process steps a1 and/or b1, and the greatest preference to the addition to process step b1.

Preference is given to adjustment, in the water/organic solvent system, to a pH of 4.5 to a maximum of pH 8.5, since great degradation of the propyl gallate is detected at higher pH values. Especially preferably, a pH of 6.5 to a maximum of pH 8.5 is chosen for the system.

Preferred embodiments with regard to the vitamins can be found in the elucidations at the outset.

The organic solvents used in stage a1) of the process of the invention are in particular water-miscible, thermally stable, volatile solvents comprising solely carbon, hydrogen and oxygen, such as alcohols, ethers, esters, ketones or acetals. Appropriately, those solvents that are water-miscible at least to an extent of 10%, have a boiling point below 200'C and/or have fewer than 10 carbon atoms are used. Particular preference is given to using methanol, ethanol, n-propanol, isopropanol, butane-1,2-diol 1-methyl ether (1-methoxybutan-2-ol), propane-1,2-diol 1-n-propyl ether (1-propoxypropan-2-ol), tetrahydrofuran, acetone or mixtures thereof.

Colloids used in the process are plant gums, modified plant gums, gelatin, modified gelatin, starch, modified starch, lignosulfonate, chitosan, carrageenan, casein, caseinate, whey protein, zein, modified cellulose, pectin, modified pectin, plant proteins and modified plant proteins or mixtures thereof.

According to the invention, plant gums are understood here to mean agar, alginic acid, alginate, chicle, dammar, marshmallow extracts, gellan, guar flour, gum arabic, gum from plantain seed husk, gum from spruce tree sap, carob flour, karaya, konjac flour, mastic, tara gum, tragacanth, xanthan.

Preference is given in accordance with the invention to gelatin and/or plant gums and/or modified plant gums.

To increase the mechanical stability of the dry product, it is appropriate to add a plasticizer to the colloid, such as polyols, sugars or sugar alcohols, e.g. sucrose, glucose, glucose syrup, starch hydrolyzates, fructose, fructose syrup, lactose, maltose, xylose, arabinose, ribose, trehalose, invert sugar, sorbitol, mannitol, dextrin, maltodextrin, glycerol, polyether glycols or isomalt. The name isomalt denotes a sugar substitute which is also supplied under the Palatinit® tradename (Südzucker, Germany). Isomalt is a hydrogenated isomaltulose which consists of roughly equal portions of 6-O-α-D-glucopyranosyl-D-sorbitol and 1-O-α-D-glucopyranosyl-D-mannitol. Plasticizers used with preference are sucrose, glucose syrup and lactose.

The pulverulent vitamin formulation of the invention optionally also comprises emulsifiers which, in selected cases, are used with preference in the production of the dispersion for stabilization of the phases in the production of the active ingredient formulation of the invention. Examples are mono- and diglycerides, monoglycerol fatty acid esters, polyglycerol fatty acid esters, sorbitan fatty acid esters, propylene glycol fatty acid esters, monoglycerol citric acid esters, sugar fatty acid esters or lecithin. Emulsifiers used with preference are mono- and diglycerides, monoglycerol fatty acid esters and lecithin.

Under some circumstances, it may also be advantageous additionally to use a physiologically approved oil of animal or vegetable origin, for example sesame oil, maize kernel oil, cottonseed oil, soybean oil, peanut oil, sunflower oil, rapeseed oil, coconut oil, palm oil, olive oil, safflower oil, animal fats, lard, tallow, oils modified by hydrogenating, fractionating or transesterifying, or mixtures thereof. Preferred oils are maize kernel oil, sunflower oil and rapeseed oil.

It may additionally be advantageous to add metal chelators, such as EDTA and citric acid, in the process.

The ratio of colloid and plasticizer to carotenoid solution is generally chosen such that a dry product that comprises between 2% and 25% by weight of a vitamin, 10% to 50% by weight of a colloid, 20% to 70% by weight of a plasticizer and 3.5% to 9.5% by weight of propyl gallate, optionally appropriate amounts of tocopherol or BHT, and 0.1% to 60% by weight of auxiliaries and additives is obtained, where the sum total of the percentages of all components of the formulation is 100% by weight.

The tocopherol is preferably added to the organic solvent process step a1), where the ratio of propyl gallate to tocopherol according to the invention is 9:1 to 1:2, preferably 2:1 to 1:1. In the case of addition of tocopherol, preference is given in accordance with the invention to using natural tocopherol.

If BHT is added, it is preferably added in accordance with the invention to the dispersion, i.e. In process step c1, after removal of the solvents. According to the invention, the ratio of propyl gallate to BHT is 8:1 to 1:4, preferably 2:1 to 1:3.

According to the invention, in step c1) of the process, the dispersion formed is converted to a dry powder by removing the solvent or mixture and then drying. It is advantageous, prior to the removal of the solvent or solvent mixture, to lower the pH of the dispersion formed with sulfuric acid to a range from 6.5 to 7, especially to pH 6.8; subsequently, the conversion to a dry powder can then be effected, inter alia, by spray drying, spray cooling, modified spray drying, freeze-drying or drying in a fluidized bed, optionally also in the presence of a separating agent. The preferred separating agent here is selected from the group consisting of silicon dioxide, hydrophobically modified silica, tricalcium phosphate (TCP), calcium carbonate, sodium carbonate, potassium carbonate, magnesium carbonate, calcium oxide, magnesium oxide, dicalcium diphosphate, calcium silicate, magnesium silicate, magnesium trisilicate, sodium aluminum silicate, talc, kaolin, calcium stearate, magnesium stearate, starches from various botanical sources, cellulose or mixtures thereof. Particular preference is given here to silicon dioxide, tricalcium phosphate (TCP), hydrophobically modified silica and cornstarch.

Preferably, in process step c1), the dispersion formed is concentrated to a solids concentration of about 25% to 50% by weight by distillative removal of the majority of the solvent or mixture, and then this concentrated dispersion is converted to a dry powder in a spray drier.

More preferably, in process step c1) of the process of the invention, the drying is conducted in a spray drier with an integrated and/or downstream external fluidized bed. What is preferably formed here is a pulverulent formulation with agglomerated particles.

An alternative process for producing the formulation of the invention is to dissolve the vitamin, in a process step a2), in a volatile, water-immiscible organic solvent at temperatures of 30 to 150° C., optionally under elevated pressure, and then to emulsify this solution, in a process step b2), in an aqueous solution of a colloid. Then, in process step c2), the volatile organic solvent is removed from the resultant emulsion in a manner known per se, for example by distillation, optionally with employment of reduced pressure, giving a dispersion that can be converted to a dry powder by removal of the water and subsequent drying.

In the context of the present invention, the term "a water-immiscible organic solvent" means an organic solvent having a water solubility at standard pressure of less than 10%. Possible solvents here include halogenated aliphatic hydrocarbons, for example methylene chloride, chloroform and carbon tetrachloride, carboxylic esters such as dimethyl carbonate, diethyl carbonate, propylene carbonate, ethyl formate, methyl, ethyl or isopropyl acetate, and ethers, such as methyl tert-butyl ether, and corresponding mixtures of the solvents mentioned.

If the vitamin, owing to its low melting point, should already be in liquid form at room temperature (20° C.) under standard pressure or have a melting point below 100° C., or be in the form of a solution in an oil, as a further configuration of the process, it is possible to emulsify the vitamin in an aqueous solution of a colloid directly or after melting, or dissolved in oil (process step a3) without using organic solvents, and then to convert it to a dry powder by removing the water and then drying (c3).

In these two alternative processes too, the addition of propyl gallate is advantageous. Analogously to the remarks made for processes a1-c1, it is added at 3.5% to 9.5% by weight based on the total amount of the formulation. In the former alternative process, the propyl gallate can be added to the aqueous colloid phase, i.e. in process step b2, to the vitamin-comprising organic solvent (in process step a2) and/or to the dispersion (process step c2), preference being given to the addition of the propyl gallate to the aqueous colloid phase and/or to the vitamin-comprising organic solvent, and the greatest preference to the addition to process step b2.

If the vitamin is in the form of oil or in molten form or dissolved in an oil, the propyl gallate is added to the vitamin (process step a3) and/or to the aqueous colloid phase (process step b3) and/or to the dispersion (process step c3). The addition of the propyl gallate to the aqueous colloid phase is the most preferred here.

With regard to pH adjustment, it should be noted that, if the propyl gallate is added to the organic solvent or to the vitamin in oil form or in molten form or dissolved in oil, this pH adjustment is undertaken in the aqueous colloid phase.

Useful oils for dissolution of the vitamins include the physiologically approved oils of animal or vegetable origin that are mentioned in the application. Preferred oils for this purpose are maize kernel oil, sunflower oil and rapeseed oil.

Colloids used in the process are plant gums, modified plant gums, gelatin, modified gelatin, starch, modified starch, lignosulfonate, chitosan, carrageenan, casein, caseinate, whey protein, zein, modified cellulose, pectin, modified pectin, plant proteins and modified plant proteins or mixtures thereof.

To increase the mechanical stability of the vitamin formulation, it is appropriate to add a plasticizer to the colloid during the process. Suitable for this purpose are polyols, sugars or sugar alcohols, e.g. sucrose, glucose, glucose syrup, starch hydrolyzates, fructose, fructose syrup, lactose, maltose, xylose, arabinose, ribose, trehalose, invert sugar, sorbitol, mannitol, dextrin, maltodextrin, glycerol, polyether glycols or isomalt. The name isomalt denotes a sugar substitute which is also supplied under the Palatinit® tradename (Südzucker, Germany). Isomalt is a hydrogenated isomaltulose which consists of roughly equal portions of 6-O-α-D-glucopyranosyl-D-sorbitol and 1-O-α-D-glucopyranosyl-D-mannitol. Plasticizers used with preference are sucrose, glucose syrup and lactose.

In addition, emulsifiers may be used to stabilize the phases in the production of the active ingredient formulation of the invention, for example mono- and diglycerides, monoglycerol fatty acid esters, polyglycerol fatty acid esters, sorbitan fatty acid esters, propylene glycol fatty acid esters, monoglycerol citric acid esters, sugar fatty acid esters or lecithin. Emulsifiers used with preference are mono- and diglycerides, monoglycerol fatty acid esters and lecithin.

Under some circumstances, it may also be advantageous additionally to use a physiologically approved oil of animal or vegetable origin, for example sesame oil, maize kernel oil, cottonseed oil, soybean oil, peanut oil, sunflower oil, rapeseed oil, coconut oil, palm oil, olive oil, safflower oil, animal fats, lard, tallow, oils modified by hydrogenating, fractionating or transesterifying, or mixtures thereof. Preferred oils are maize kernel oil, sunflower oil and rapeseed oil.

It may additionally be advantageous to add metal chelators, such as EDTA and citric acid, in the process.

The ratio of colloid and plasticizer to carotenoid solution in the process is generally chosen such that a dry product that comprises between 2% and 25% by weight of a vitamin, 10% to 50% by weight of a colloid, 20% to 70% by weight of a plasticizer and 3.5% to 9.5% by weight of propyl gallate, optionally appropriate amounts of tocopherol or BHT, and 0.1% to 60% by weight of auxiliaries and additives is obtained, where the sum total of the percentages of all components of the formulation is 100% by weight.

The tocopherol is preferably added to the organic solvent process step a), where the ratio of propyl gallate to tocopherol according to the invention is 9:1 to 1:2, preferably 2:1 to 1:1. In the case of addition of tocopherol, preference is given in accordance with the invention to using natural tocopherol.

If BHT is added, it is preferably added in accordance with the invention to the dispersion, i.e. in process step c, after removal of the solvents. According to the invention, the ratio of propyl gallate to BHT is 8:1 to 1:4, preferably 2:1 to 1:3.

In the process of the invention, in process step c2), the emulsion formed is converted to a dispersion by removing the organic solvent or mixture and then converted to a dry powder by removing the water with a subsequent drying step. It is advantageous, prior to the removal of the water, to lower the pH of the dispersion formed with sulfuric acid to a range from 6.5 to 7, especially to pH 6.8; subsequently, the conversion to a dry powder can then be effected, inter alia, by spray drying, spray cooling, modified spray drying, freeze-drying or drying in a fluidized bed, optionally also in the presence of a coating material. Suitable coating materials include cornstarch, silica, modified silica, tricalcium phosphate (TCP), calcium carbonate, sodium carbonate, potassium carbonate, magnesium carbonate, calcium oxide, magnesium oxide, dicalcium diphosphate, calcium silicate, magnesium silicate, magnesium trisilicate, sodium aluminum silicate, talc, kaolin, calcium stearate, magnesium stearate, starches from various botanical sources, cellulose or mixtures thereof. Particular preference is given here to silicon dioxide, tricalcium phosphate (TCP), hydrophobically modified silica and cornstarch.

Preferably, in process step c2), the dispersion formed is concentrated to a solids concentration of about 25% to 50% by weight by distillative removal of the majority of the solvent or mixture, and then this concentrated dispersion is converted to a dry powder in a spray drier.

More preferably, in process step c2) of the process of the invention, the drying is conducted in a spray drier with an integrated and/or downstream external fluidized bed. What is preferably formed here is a pulverulent formulation with agglomerated particles.

Except for the removal of the organic solvent which is unnecessary in process step c3), the process measures c2) with the preferences mentioned are also applicable to process step c3).

The pulverulent formulation of the invention is suitable, inter alia, as additive to food preparations, for example for coloring foods such as drinks, as means for producing pharmaceutical and cosmetics preparations, and also for producing food supplement formulations, for example multivitamin formulations in the human and animal sectors.

The present invention further provides the use of the above-described pulverulent formulation of the invention as additive to animal feeds, foods, food supplements, personal care products or pharmaceutical compositions.

The present invention likewise provides animal feeds, foods, food supplements, personal care products or pharmaceutical compositions comprising the pulverulent formulation of the invention.

The invention is elucidated by the examples which follow, but do not restrict the invention in any way:

EXAMPLES

Example 1 (Example 7 from Table 1)

30 g of citranaxanthin were suspended in 240 g of isopropanol together with 1.1 g of ascorbyl palmitate and, with setting of the pressure-limiting valve to 30 bar, mixed continuously with 390 g of isopropanol in a mixing chamber A. At a metering rate of 6 L/h on the suspension side and of 9 L/h on the solvent side, a mixing temperature of 170° C. was established in the mixing chamber A. After a residence time of 0.3 second, the molecularly disperse solution was mixed in mixing chamber B with a solution of 32 g of gelatin, 71.4 g of sucrose and 50 g of glucose syrup in 4000 g of water at a throughput rate of 100 L/h. After the solvent had been removed under reduced pressure in a distillation apparatus, an active ingredient dispersion was obtained, to which 8 g of sunflower oil and 8 g of propyl gallate were added. The propyl gallate was predissolved here in 200 mL of water and adjusted to pH 7 with NaOH. Subsequently, the dispersion was converted to a stable, water-soluble dry powder by spray drying. After dissolution in water, by photon correlation spectroscopy (PCS), a particle size of 386 nm (standard deviation 142.5, polydispersity index PDI 0.185, D(95): 660 nm) was measured (Malvern Zetasizer Nano ZSP).

Stability Test for Citranaxanthin

The stability of the particles thus produced was tested in a stress test. For this purpose, specimens each of 100 mg of the particles produced and 4 g of premix mixture were weighed into 50 mL glass bottles. The premix mixture consisted of 50% by weight of fine lime (particle size <1000 µm), 20% by weight of wheat bran (particle size <1000 µm), 20% by weight of 50% silica-supported choline chloride (particle size <1000 µm) and 10% by weight of trace element mixture (particle size 100-500 µm), and the trace element mixture of 46.78% by weight of $FeSO_4 \times 7H_2O$ (100-500 µm), 37.43% by weight of $CuSO_4 \times 5H_2O$ (100-500 µm), 11.79% by weight of ZnO (<500 µm), 3.61% by weight of MnO and 0.39% by weight of $CoCO_3$. After addition of all ingredients, the specimens were carefully mixed by hand. These specimens were stored in a climate-controlled chamber at 40° C. and 70% air humidity for 4 weeks. Prior to commencement of the storage and after completion of the storage, the citranaxanthin content of the specimens was determined. The ratio of the citranaxanthin contents after and prior to storage was used to calculate the retention.

The retention values of the examples are compiled in the table which follows.

TABLE 1

| | Active ingredient | Antioxidant | Antioxidant [% by wt.] | Site of antioxidant addition | Retention Active ingredient content after 4-week test [%] |
|---|---|---|---|---|---|
| 1 | Citranaxanthin | — | 0 | Dispersion | 7.9 |
| 2 | Citranaxanthin | Ethoxyquin | 4 | added in solid form to the dispersion, no pH adjustment | 52.6 |

TABLE 1-continued

| Active ingredient | Antioxidant | Antioxidant [% by wt.] | Site of antioxidant addition | Retention Active ingredient content after 4-week test [%] |
|---|---|---|---|---|
| 3 Citranaxanthin | BHA | 4 | Molten BHA was stirred into the dispersion at 10 000 rpm by Ultraturrax for 2 minutes and this was then introduced 5× via the microfluidizer at 1000 bar | 8.2 |
| 4 Citranaxanthin | Na ascorbate | 4 | added in solid form to the dispersion, no pH adjustment | 2.4 |
| 5 Citranaxanthin | Methylhydroquinone | 4 | added in solid form to the dispersion, no pH adjustment | 10.2 |
| 6 Citranaxanthin | Vitamin E TPGS | 4 | Added to the dispersion as a 10% solution without pH adjustment | 2.2 |
| 7 Citranaxanthin | Propyl gallate | 4 | Dissolved in water pH 7 (4% by weight solution) and added to the dispersion | 47.8 |
| 8 Citranaxanthin | Lauryl gallate | 4 | Addition to the active ingredient phase, no pH adjustment | 15.9 |
| 9 Citranaxanthin | Green tea extract | 4 | Dissolved in water pH 7 and added to the dispersion | 19.4 |
| 10 Citranaxanthin | Rosmarinic acid | 4 | Added to the dispersion as a 10% solution without pH adjustment | 14 |

The higher the retention, the better the stability of the particles or preparation thereof.

Example 2

Effect of pH on Propyl Gallate Activity

The experiments show that an optimal pH range for the propyl gallate addition is in the range from pH 4.5 up to and including pH 8.5. Even short residence times at pH values greater than 8.5 or predissolution of the propyl gallate at such pH values were sufficient to significantly restrict the activity of propyl gallate.

TABLE 2a

Effect of pH in the propyl gallate-containing dispersion on citranaxanthin stability.

| Active ingredient | Propyl gallate [% by wt.] | Site of propyl gallate addition | pH of sprayed dispersion | Retention (active constituent after 4 weeks in the test) [%] |
|---|---|---|---|---|
| Citranaxanthin | 4 | Dispersion | 4.5 | 42.2 |
| Citranaxanthin | 4 | Dispersion | 6 | 39.1 |
| Citranaxanthin | 4 | Dispersion | 7 | 47.8 |
| Citranaxanthin | 4 | Dispersion | 8 | 49.4 |
| Citranaxanthin | 4 | Dispersion | 9 | 28.2 |
| Citranaxanthin | 4 | Dispersion | 10 | 36.4 |
| Citranaxanthin | 4 | Dispersion | 11 | 14.7 |

This result is also confirmed when the propyl gallate is added not to the vitamin-comprising dispersion, but the propyl gallate is already added to the protective colloid phase (table 2b). A very good result is found when the propyl gallate is added to the protective colloid phase, this is adjusted from a pH of 5 to 7 to a pH of 7 with NaOH, and the pH is raised to 8 to 8.5 with NaOH only 15 to 30 minutes prior to the precipitation.

TABLE 2b

Effect of pH in the propyl gallate-containing protective colloid phase on citranaxanthin stability.

| Active ingredient | Propyl gallate [% by wt.] | Site of propyl gallate addition | pH of the colloid phase | Retention Active ingredient content after 4-week test [%] |
|---|---|---|---|---|
| Citranaxanthin | 4 | Colloid phase | Preadjustment to 7; then adjustment to pH 8.5 at maximum | 44.1 |
| Citranaxanthin | 4 | Colloid phase | 8.5-9.5 | 13.4 |

The mode of addition of the propyl gallate (in solid form or dissolved in water pH 7) to the vitamin-comprising dispersion, by contrast, has no effect on citranaxanthin stability (table 2c).

TABLE 2c

Study of the mode of addition of propyl gallate on retention

| Active ingredient | Propyl gallate [% by wt.] | Site of propyl gallate addition | Mode of addition of PG | Retention Active ingredient content after 4-week test [%] |
|---|---|---|---|---|
| Citranaxanthin | 4 | Dispersion | Dissolved in water pH 7 | 47.8 |
| Citranaxanthin | 4 | Dispersion | Dissolved in water pH 7 | 46 |
| Citranaxanthin | 4 | Dispersion | Dissolved in water pH 7 | 49.4 |
| Citranaxanthin | 4 | Dispersion | Addition in solid form without pre-dissolution | 47.2 |
| Citranaxanthin | 4 | Dispersion | Addition in solid form without pre-dissolution | 44.9 |

Example 3

Effect of Propyl Gallate Concentration on Active Ingredient Stability a). Increasing the propyl gallate concentration increases the stability of the citranaxanthin active ingredient. However, surprisingly, in the case of an increase in the propyl gallate in the formulation to 10% by weight, a significant decline in stability is observed. A very good stabilizing effect was observed at 4% to 9% by weight of propyl gallate in the formulation, preferably 7% to 9% by weight, with an optimum at 8% to 9% by weight (table 3a).

TABLE 3a

Effect of propyl gallate concentration on active ingredient stability of citranaxanthin

| Active ingredient | Propyl gallate [% by wt.] | Site of propyl gallate addition | Retention Active ingredient content after 4-week test [%] |
|---|---|---|---|
| Citranaxanthin | 0 | Dispersion | 7.9 |
| Citranaxanthin | 2 | Dispersion | 20.2 |
| Citranaxanthin | 3 | Dispersion | 26.7 |
| Citranaxanthin | 4 | Dispersion | 47.8 |
| Citranaxanthin | 5 | Dispersion | 45.7 |
| Citranaxanthin | 6 | Dispersion | 45.9 |
| Citranaxanthin | 7 | Dispersion | 49.5 |
| Citranaxanthin | 8 | Dispersion | 55.9 |
| Citranaxanthin | 8.5 | Dispersion | 51.9 |
| Citranaxanthin | 9 | Dispersion | 57.4 |
| Citranaxanthin | 10 | Dispersion | 19.6 |

The positive effect of propyl gallate, and also the concentration optimum, can also be confirmed for other carotenoids. (Tables 3b-e).

b). 30 g of canthaxanthin were suspended in 240 g of isopropanol together with 1.1 g of ascorbyl palmitate and, with setting of the pressure-limiting valve to 30 bar, mixed continuously with 390 g of isopropanol in a mixing chamber A. At a metering rate of 6 L/h on the suspension side and of 9 L/h on the solvent side, a mixing temperature of 170° C. was established in the mixing chamber A. After a residence time of 0.3 second, the molecularly disperse solution was mixed in mixing chamber B with a solution of 32 g of gelatin and 121.4 g of sucrose in 4000 g of water at a throughput rate of 100 L/h. After removal of the solvent under reduced pressure in a distillation apparatus, an active ingredient dispersion was obtained, to which 8 g of sunflower oil and the amounts of propyl gallate specified in table 3b in each case were added. The propyl gallate was predissolved here in 200 mL of water and adjusted to pH 7 with NaOH. Subsequently, the dispersion was converted to a stable, water-soluble dry powder by spray drying. After dissolution in water, by PCS, a particle size of 290 nm (standard deviation 140, polydispersity index PDI 0.193, D(95): 594 nm) was measured (Malvern Zetasizer Nano ZSP).

TABLE 3b

Effect of propyl gallate concentration on active ingredient stability of canthaxanthin

| Active ingredient | Propyl gallate [%] | Site of propyl gallate addition | Retention Active ingredient content after 4-week premix test [%] |
|---|---|---|---|
| Canthaxanthin | 4 | Dispersion | 61.2 |
| Canthaxanthin | 6 | Dispersion | 77.9 |
| Canthaxanthin | 8 | Dispersion | 83.3 |
| Canthaxanthin | 9 | Dispersion | 82.4 |
| Canthaxanthin | 10 | Dispersion | 69.8 |
| Canthaxanthin | 12 | Dispersion | 47.2 | c). 30 g of C30 ester were suspended in 240 g of isopropanol together with 1.1 g of ascorbyl palmitate and, with setting of the pressure-limiting valve to 30 bar, mixed continuously with 390 g of isopropanol in a mixing chamber A. At a metering rate of 6 L/h on the suspension side and of 9 L/h on the solvent side, a mixing temperature of 170'C was established in the mixing chamber A. After a residence time of 0.3 second, the molecularly disperse solution was mixed in mixing chamber B with a solution of 32 g of gelatin and 121.4 g of sucrose in 4000 g of water at a throughput rate of 100 L/h. After the solvent had been removed under reduced pressure in a distillation apparatus, an active ingredient dispersion was obtained, to which 8 g of sunflower oil and the amounts of propyl gallate specified in table 3c in each case in % by weight were added. The propyl gallate was predissolved here in 200 mL of water and adjusted to pH 7 with NaOH. Subsequently, the dispersion was converted to a stable, water-soluble dry powder by spray drying. After dissolution in water, by PCS, a particle size of 280 nm (standard deviation 120, polydispersity index PDI 0.181) was measured (Malvern Zetasizer Nano ZSP).

TABLE 3c

Effect of propyl gallate concentration on active ingredient stability of C30 ester

| Active ingredient | Propyl gallate [% by wt.] | Site of propyl gallate addition | Retention Active ingredient content after 4-week premix test [%] |
|---|---|---|---|
| C30 ester | 0 | Dispersion | 6.7 |
| C30 ester | 2 | Dispersion | 13.83 |
| C30 ester | 4 | Dispersion | 42.7 |
| C30 ester | 6 | Dispersion | 57.7 |
| C30 ester | 8 | Dispersion | 64.1 |
| C30 ester | 10 | Dispersion | 58.5 |
| C30 ester | 12 | Dispersion | 54.3 | d). 30 g of β-carotene were suspended in 240 g of isopropanol together with 1.1 g of ascorbyl palmitate and, with setting of the pressure-limiting valve to 30 bar, mixed continuously with 390 g of isopropanol in a mixing chamber A. At a metering rate of 6 L/h on the suspension side and of 9 L/h on the solvent side, a mixing temperature of 170° C. was established in the mixing chamber A. After a residence time of 0.3 second, the molecularly disperse solution was mixed in mixing chamber B with a solution of 32 g of gelatin, 71.4 g of sucrose and 50 g of glucose syrup in 4000 g of water at a throughput rate of 100 L/h. After the solvent had been removed under reduced pressure in a distillation apparatus, an active ingredient dispersion was obtained, to which 8 g of sunflower oil and 8 g of propyl gallate were added. The propyl gallate was predissolved here in 200 mL of water and adjusted to pH 7 with NaOH. Subsequently, the dispersion was converted to a stable, water-soluble dry powder by spray drying. After dissolution in water, by PCS, a particle size of 262 nm (standard deviation 182, polydispersity index PDI 0.268) was measured (Malvern Zetasizer Nano ZSP).

TABLE 3d

Comparison of the stabilities of ethoxyquin and propyl gallate on β-carotene.

| Active ingredient | Antioxidant | Antioxidant [% by wt.] | Site of antioxidant addition | Retention Active ingredient content after 4-week test [%] |
|---|---|---|---|---|
| β-carotene | Ethoxyquin | 4 | Dispersion | 22.2 |
| β-carotene | Propyl gallate | 4 | Dispersion | 30.3 | e). 30 g of C30 ester were suspended in 240 g of isopropanol together with 1.1 g of ascorbyl palmitate and, with setting of the pressure-limiting valve to 30 bar, mixed continuously with 390 g of isopropanol in a mixing chamber A. At a metering rate of 6 L/h on the suspension side and of 9 L/h on the solvent side, a mixing temperature of 170° C. was established in the mixing chamber A. After a residence time of 0.3 second, the molecularly disperse solution was mixed in mixing chamber B with a solution of 32 g of gelatin and 121.4 g of sucrose in 4000 g of water at a throughput rate of 100 L/h. After the solvent had been removed under reduced pressure in a distillation apparatus, an active ingredient dispersion was obtained, to which 8 g of sunflower oil and the amounts of propyl gallate specified in table 3e in each case in % by weight were added. The propyl gallate was predissolved here in 200 mL of water and adjusted to pH 7 with NaOH. Subsequently, the dispersion was converted to a stable, water-soluble dry powder by spray drying. After dissolution in water, by PCS, a particle size of 373 nm (standard deviation 165, polydispersity index PDI 0.203, D(95): 683 nm) was measured (Malvern Zetasizer Nano ZSP).

TABLE 3e

Comparison of the stabilities of ethoxyquin and propyl gallate on C-30 ester.

| Active ingredient | Antioxidant | Antioxidant [% by wt.] | Site of antioxidant addition | Retention Active ingredient content after 4-week test [%] |
|---|---|---|---|---|
| C30 ester | Ethoxyquin | 4 | Dispersion | 28.6 |
| C30 ester | Propyl gallate | 4 | Dispersion | 33.4 |
| C30 ester | Propyl gallate | 4 | Dispersion (pH adjustment before spraying from pH 8.5 to pH 6.8 with H$_2$SO$_4$) | 39.8 |

TABLE 3e-continued

Comparison of the stabilities of ethoxyquin and propyl gallate on C-30 ester.

| Active ingredient | Antioxidant | Antioxidant [% by wt.] | Site of antioxidant addition | Retention Active ingredient content after 4-week test [%] |
|---|---|---|---|---|
| C30 ester | Propyl gallate | 6 | Dispersion | 44.4 |
| C30 ester | Propyl gallate | 8 | Dispersion | 43.4 |

Example 4

Effect of Mixed Tocopherol and D,L α-Tocopherol on Stabilities

Owing to their poor water solubility, the tocopherols originating from synthetic and natural sources are dissolved in the phase comprising the active ingredient. If solely natural or synthetic tocopherol is added on its own in each case, there is no difference in their protective effect as antioxidant and in their stabilization of the carotenoids or retinoids.

TABLE 4a

Effect of the synthetic and natural tocopherols on stability

| Active ingredient | Antioxidant | Antioxidant [% by wt.] | Site of antioxidant addition | Retention Active ingredient content after 4-week test [%] |
|---|---|---|---|---|
| Canthaxanthin | Mixed tocopherol | 4 | Active ingredient phase | 48.7 |
| Canthaxanthin | D,L-α Tocopherol | 4 | Active ingredient phase | 45.7 |

The situation is different when propyl gallate is additionally added as antioxidant to the tocopherols. In this case, the stabilization in the premix test for the combination of mixed tocopherol/propyl gallate is much more marked than for the combination of D,L alpha-tocopherol with propyl gallate (table 4b).

TABLE 4b

Effect of the combination of synthetic or natural tocopherols with propyl gallate on the stabilities of vitamins.

| Active ingredient | Antioxidant | Antioxidant [% by wt.] | Retention Active ingredient content after 4-week test |
|---|---|---|---|
| Canthaxanthin | Mixed tocopherol (in active ingredient phase) + | 4 | 78.1 |
|  | Propyl gallate (in protective colloid phase) | 4 |  |
| Canthaxanthin | D,L-α Tocopherol (in active ingredient phase) + | 4 | 57.2 |
|  | Propyl gallate (in protective colloid phase) | 4 |  |

TABLE 4b-continued

Effect of the combination of synthetic or natural tocopherols with propyl gallate on the stabilities of vitamins.

| Active ingredient | Antioxidant | Antioxidant [% by wt.] | Retention Active ingredient content after 4-week test |
|---|---|---|---|
| C30 ester | Mixed tocopherol (in active ingredient phase) + | 4 | 57.5 |
|  | Propyl gallate (in protective colloid phase) | 4 |  |
| C30 ester | D,L-α Tocopherol (in active ingredient phase) + | 4 | 29.2 |
|  | Propyl gallate (in protective colloid phase) | 4 |  |
| Citranaxanthin | Mixed tocopherol (in active ingredient phase) + | 4 | 67.5 |
|  | Propyl gallate (in protective colloid phase) | 4 |  |
| Citranaxanthin | D,L-α Tocopherol (in active ingredient phase) + | 4 | 21.3 |
|  | Propyl gallate (in protective colloid phase) | 4 |  |

Example 5 a). Synergistic Effect Between Propyl Gallate and Tocopherol

For the combination of propyl gallate with tocopherol, it has been found that, for this system, the total concentration of antioxidant in the formulation can be reduced without losing stability. If the stabilities for the formulation comprising 4% propyl gallate (61.2%) and that comprising 4% mixed tocopherol (48.7%) are compared with one another, for this system, the propyl gallate is clearly the better antioxidant. If, by contrast, 4% propyl gallate is mixed with 4% mixed tocopherol and the stability thereof (80.3%) is compared with that comprising 8% propyl gallate (83.3%), a synergistic effect that would not have been expected from the individual values is apparent. This becomes even more noticeable when, with constant propyl gallate content, the concentration of mixed tocopherol is reduced from 4% to 2%. For this system, a stability of 80.6% is measured, whereas, for a system comprising 6% propyl gallate, only a stability of 71.3% is obtained. This shows clearly that only a particular concentration of mixed tocopherol is required to obtain a significant rise in stability with reduced antioxidant content in the formulation.

TABLE 5a

Combination of mixed tocopherol with propyl gallate.

| Active ingredient | Propyl gallate [% by wt.] | Mixed tocopherol [% by wt.] | Retention Canthaxanthin after 4-week test [%] |
|---|---|---|---|
| Canthaxanthin | 4 | 0 | 61.2 |
| Canthaxanthin | 6 | 0 | 71.3 |
| Canthaxanthin | 8 | 0 | 83.3 |
| Canthaxanthin | 0 | 4 | 48.7 |
| Canthaxanthin | 4 | 4 | 80.3 |
| Canthaxanthin | 4 | 2 | 80.8 |

2% by weight of mixed tocopherol in combination with 4% by weight of propyl gallate almost reaches the stability value for 4% by weight of mixed tocopherol in combination with 4% by weight of propyl gallate. If, however, the proportion of mixed tocopherol is reduced to 1% by weight, again in combination with 4% by weight of propyl gallate, the stability values begin to fall (table 5b).

TABLE 5b

Combination of mixed tocopherol with propyl gallate.

| Active ingredient | Propyl gallate [% by wt.] | Mixed tocopherol [% by wt.] | Retention Canthaxanthin after 4-week test [%] |
|---|---|---|---|
| Canthaxanthin | 4 (in protective colloid phase pH 7) | 2 (in active ingredient phase) | 76 |
| Canthaxanthin | 4 (in protective colloid phase pH 7) | 4 (in active ingredient phase) | 80.6 |
| Canthaxanthin | 4 (in protective colloid phase pH 7) | 1 (in active ingredient phase) | 72.8 |

TABLE 5c

Combination of mixed tocopherol with propyl gallate

| Active ingredient | Propyl gallate [% by wt.] | Mixed tocopherol [% by wt.] | Retention Canthaxanthin after 4-week test [%] |
|---|---|---|---|
| C30 ester | 4 | 0 | 42.7 |
| C30 ester | 0 | 4 | 11 |
| C30 ester | 4 | 4 | 61.7 |
| Citranaxanthin | 4 | 0 | 39.1 |
| Citranaxanthin | 0 | 4 | 10.8 |
| Citranaxanthin | 4 | 4 | 66.5 |

Experimental Method for the Addition of 4% by Weight of Propyl Gallate and 4% by Weight of Tocopherol 30 g of citranaxanthin were suspended in 240 g of isopropanol together with 1.1 g of ascorbyl palmitate and 9 g of mixed tocopherol and, with setting of the pressure-limiting valve to 30 bar, mixed continuously with 390 g of isopropanol in a mixing chamber A. At a metering rate of 6 L/h on the suspension side and of 9 L/h on the solvent side, a mixing temperature of 170'C was established in the mixing chamber A. After a residence time of 0.3 second, the molecularly disperse solution was mixed in mixing chamber B with a solution, adjusted to pH 9, of 32 g of gelatin, 71.4 g of sucrose, 50 g of glucose syrup and 9 g of propyl gallate in 4100 g of water at a throughput rate of 100 L/h. After the solvent had been removed under reduced pressure in a distillation apparatus, an active ingredient dispersion was obtained, to which 9 g of sunflower oil were added. Subsequently, the dispersion was converted to a stable, water-soluble dry powder by spray drying. After dissolution in water, by PCS, a particle size of 280 nm (standard deviation 142.5, polydispersity index PDI 0.185) was measured (Malvern Zetasizer Nano ZSP).

b). Synergistic Effect Between Propyl Gallate and BHT

TABLE 5d

Combination of BHT with propyl gallate.

| Active ingredient | Propyl gallate [% by wt.] | BHT [% by wt.] | Retention Canthaxanthin after 4-week test [%] |
|---|---|---|---|
| Citranaxanthin | 4 | 0 | 61.2 |
| Citranaxanthin | 4 | 4 | 82.3 |
| Citranaxanthin | 0 | 4 | 56.1 |
| Citranaxanthin | 0 | 4 | 65.5 |
| Citranaxanthin | 0 | 4 | 67.9 |
| Citranaxanthin | 4% by wt. of ethoxyquin | | 79.3 |

Experimental Method for the Addition of 4% by Weight of Propyl Gallate and 4% by Weight of Butylhydroxytoluene 30 g of citranaxanthin are suspended in 240 g of isopropanol together with 1.1 g of ascorbyl palmitate and, with setting of the pressure-limiting valve to 30 bar, mixed continuously with 390 g of isopropanol in a mixing chamber A. At a metering rate of 6 L/h on the suspension side and of 9 L/h on the solvent side, a mixing temperature of 170° C. is established in the mixing chamber A. After a residence time of 0.3 second, the molecularly disperse solution is mixed in mixing chamber B with a solution, adjusted to pH 9, of 32 g of gelatin, 71.4 g of sucrose, 50 g of glucose syrup and 9 g of propyl gallate in 4100 g of water at a throughput rate of 100 L/h. After the solvent has been removed under reduced pressure in a distillation apparatus, an active ingredient dispersion is obtained, to which 9 g of sunflower oil and 9 g of BHT dissolved therein are added.

Subsequently, the dispersion was converted to a stable, water-soluble dry powder by spray drying. After dissolution in water, by PCS, a particle size of 290 nm (standard deviation 140, polydispersity index PDI 0.180) was measured (Malvern Zetasizer Nano ZSP).

The invention claimed is:

1. A pulverulent vitamin formulation in which the vitamin has a particle size of less than 0.7 µm, wherein said formulation comprises 3.5% to 9.5% by weight of propyl gallate based on the total amount of the formulation, to stabilize the vitamin in the formulation and wherein the formulation is adjusted to a pH from 6.5 to 8.5.

2. The pulverulent vitamin formulation according to claim 1, where the weight ratio of propyl gallate to vitamin in the formulation is between 0.21 and 2.63.

3. The pulverulent vitamin formulation according to claim 1, wherein the vitamin is selected from the group consisting of vitamins D, E, K, Q derivatives thereof, coenzyme Q10 and carotenoids.

4. The pulverulent vitamin formulation according to claim 1, wherein the formulation comprises butylhydroxytoluene or synthetic and/or natural tocopherol.

5. The pulverulent vitamin formulation according to claim 4, wherein the tocopherol is natural tocopherol.

6. The pulverulent vitamin formulation according to claim 4, wherein propyl gallate and tocopherol are present in the formulation in a ratio of 9:1 to 1:2.

7. The pulverulent vitamin formulation according to claim 4, wherein propyl gallate and butylhydroxytoluene are present in the formulation in a ratio of 8:1 to 1:4.

8. The pulverulent vitamin formulation according to claim 1, wherein the quotient therein of active vitamins A2/A1 in relation to a comparative sample that comprises, rather than propyl gallate, the same amount of ethoxyquin B2/B1, after 4 weeks in a stress test, is at least 0.75, where the proportion of active vitamin is ascertained by weighing, 100 mg in each case of the formulation produced and 4 g of a mixture, of 50% by weight of fine lime having a particle size <1000 µm, 20% by weight of wheat bran having a particle size <1000 µm, 20% by weight of 50% silica-supported choline chloride having a particle size <1000 µm and 10% by weight of a trace element mixture having a particle size of 100-500 µm, said trace element mixture consisting of 46.78% by weight of $FeSO_{4x}7H_2O$ having a particle size of 100-500 µm, 37.43% by weight of $CUSO_{4x}5H_2O$ having a particle size of 100-500 µm, 11.79% by weight of ZnO having a particle size <500 µm, 3.61% by weight of MnO and 0.39% by weight of $CoCO_3$, into 50 mL glass containers, mixing the ingredients and storing them in a climate-controlled chamber at 40° C. and 70% humidity for 4 weeks, with determination of the vitamin contents A1 and B1 prior to commencement of the storage and of the vitamin contents A2 and B2 on conclusion of the storage and calculating the proportion of active vitamins from the quotients A2/A1 and B2/B1.

9. An animal feed, food, food supplement, personal care product or pharmaceutical composition comprising the pulverulent vitamin formulation according to claim 1.

10. The pulverulent vitamin formulation according to claim 1, wherein the vitamin is selected from the group consisting of vitamin E esters, tocotrienol, vitamin K1, vitamin K2, coenzyme Q10, (β-carotene, canthaxanthin, citranaxanthin, astaxanthin and ester derivatives, zeaxanthin and ester derivatives, lutein and ester derivatives, lycopene, apocarotenic acid and ester derivatives, apocarotenal and mixtures thereof.

11. The pulverulent vitamin formulation according to claim 1, wherein the vitamin is selected from the group consisting of (β-carotene, canthaxanthin, citranaxanthin, and C30 ester derivatives.

* * * * *